United States Patent
Laukkanen et al.

(12) 
(10) Patent No.: US 10,575,805 B2
(45) Date of Patent: Mar. 3, 2020

(54) MAMMOGRAPHY EXAMINATIONS

(71) Applicant: PLANMED OY, Helsinki (FI)

(72) Inventors: Tapio Laukkanen, Espoo (FI); Leo Aspelund, Helsinki (FI)

(73) Assignee: Planmeca OY, Helsinki (FI)

( * ) Notice: Subject to any disclaimer, the term of this patent is extended or adjusted under 35 U.S.C. 154(b) by 609 days.

(21) Appl. No.: 15/168,973

(22) Filed: May 31, 2016

(65) Prior Publication Data
US 2016/0270751 A1     Sep. 22, 2016

Related U.S. Application Data

(63) Continuation-in-part of application No. PCT/FI2014/050930, filed on Dec. 1, 2014.

(30) Foreign Application Priority Data

Nov. 29, 2013   (FI) ................................ 20130361
Dec. 13, 2013   (FI) ................................ 20136259

(51) Int. Cl.
*A61B 6/00*     (2006.01)
*A61B 5/05*     (2006.01)
*A61B 6/04*     (2006.01)

(52) U.S. Cl.
CPC ............ *A61B 6/502* (2013.01); *A61B 6/0414* (2013.01); *A61B 6/4435* (2013.01); *A61B 6/462* (2013.01); *A61B 6/464* (2013.01); *A61B 6/467* (2013.01); *A61B 6/0492* (2013.01); *A61B 6/56* (2013.01)

(58) Field of Classification Search
CPC ....... A61B 6/502; A61B 6/025; A61B 6/0414; A61B 6/482; A61B 6/466; A61B 6/04; A61B 6/40; A61B 6/0492; A61B 6/08; A61B 6/488
See application file for complete search history.

(56) References Cited

U.S. PATENT DOCUMENTS

| | | | |
|---|---|---|---|
| 4,674,107 A | 6/1987 | Urban et al. | |
| 6,891,920 B1 | 5/2005 | Minyard et al. | |
| 8,311,305 B2 | 11/2012 | Ohyu et al. | |
| 2003/0073895 A1 | 4/2003 | Nields et al. | |
| 2003/0091150 A1 | 5/2003 | Barber et al. | |
| 2003/0233040 A1 | 12/2003 | Sakaniwa | |

(Continued)

FOREIGN PATENT DOCUMENTS

| | | |
|---|---|---|
| CN | 102429678 B | 8/2016 |
| DE | 102007052650 A1 | 5/2009 |

(Continued)

*Primary Examiner* — Don K Wong
(74) *Attorney, Agent, or Firm* — Fay Sharpe LLP (57) ABSTRACT

The invention relates to an arrangement in connection with a mammography apparatus, in the invention, a screen or a user interface with a screen is attached to the mammography apparatus, which attachment is realized such that the screen or the user interface with a screen is aligned or can be aligned at least partly towards a lower tray structure of the mammography apparatus. Such screen or a user interface with a screen can be arranged in a functional connection with an information system and patient images recorded earlier in the information system can be displayed on the screen or the user interface with a screen.

8 Claims, 4 Drawing Sheets

(56) References Cited

U.S. PATENT DOCUMENTS

| | | | |
|---|---|---|---|
| 2004/0102699 A1* | 5/2004 | Fors | A61B 6/463 600/426 |
| 2008/0087830 A1 | 4/2008 | Kashiwagi | |
| 2010/0030078 A1 | 2/2010 | Mikami | |
| 2010/0208037 A1 | 8/2010 | Sendai | |
| 2011/0087132 A1* | 4/2011 | DeFreitas | A61B 10/0233 600/567 |
| 2012/0014505 A1 | 1/2012 | Morita et al. | |
| 2012/0016222 A1 | 1/2012 | Bouvier | |
| 2012/0053455 A1* | 3/2012 | Okada | A61B 6/00 600/427 |
| 2012/0093298 A1 | 4/2012 | Lalena | |
| 2012/0153182 A1* | 6/2012 | Iwakiri | A61B 6/4283 250/394 |
| 2012/0219108 A1* | 8/2012 | Albanese | A61B 6/02 378/22 |

FOREIGN PATENT DOCUMENTS

| | | | |
|---|---|---|---|
| EP | 2407108 A1 | 1/2012 | |
| JP | 2007236805 A | 9/2007 | |
| JP | 2008119457 A | 5/2008 | |
| JP | 2009285345 A | 12/2009 | |
| JP | 2009291336 A | 12/2009 | |
| JP | 2010167134 A | 8/2010 | |
| WO | 2015008117 A1 | 1/2015 | |

* cited by examiner

MAMMOGRAPHY EXAMINATIONS

This application is a continuation-in-part filing claiming priority to International Application No. PCT/FI2014/050930, the disclosure of which is herein incorporated by reference.

FIELD OF THE INVENTION

The present invention relates to an arrangement and method to facilitate mammography examinations.

DESCRIPTION OF PRIOR ART

Breast cancer is the most common type of cancer in women. According to investigations, about one in every ten women contracts breast cancer at some point in their lives. When breast cancer is detected on the basis of symptoms, the illness often has already developed to a stage where the prognosis for recovery is relatively poor. Some of the cases are detected in screening programs arranged in many countries for women over the age of 40. Screening often reveals a cancer at a very early stage, so its treatment can be started in time and recovery is thus more likely.

Mammography is a widely used method in breast cancer screening as a clinical investigation method and also in follow-up diagnosis. Mammography is an X-ray imaging method wherein an apparatus specifically designed for this purpose is used. In screening studies, mammography has been reported to have a sensitivity of 90-93% and a specificity of 90-97%. This indicates that screening studies are useful and that early detection of breast cancer by screening can save human lives. It has been established that mammography reduces breast cancer mortality by 35 percent among women over 50 and by 25-35 percent among women at the age of 40-50 years.

The mammography images are examined to detect various anomalies in the breast, such as calcifications, i.e. small deposits of calcium in the soft breast tissue. A calcification generally cannot be detected by feeling the breast, but it is visible in the x-ray image. Large calcifications are generally not associated with cancer, but clusters of small calcium deposits, i.e. so-called micro-calcifications, are an indication of extra breast cell activity, which may be associated with breast cancer. Other features to be detected by mammography include cysts and fibroadenomas, which, however, are generally not associated with cancer.

In conventional screening mammography, the breast gland is typically compressed between two compression plates and exposed to radiation at least twice, from above and from an oblique direction. If necessary, an additional third image is taken squarely from the side. As in such imaging the tissue layers lie on top of each other in the direction of the x-ray beam, these irradiations produce two-dimensional images in which strongly absorbing structures may hinder the detection of structures lying beneath them.

Continual improvement in mammography has led to novel type of mammography methods and devices that produce tomographic images of a patient's breast. In these solutions, several projections of the breast at different angles are produced and an image is generated by using an applicable reconstruction algorithm. From the image information, i.e. from the individual images, typically several images are constructed which represent layers of the breast oriented in parallel with the surface of the x-ray detector, thus making possible to detect tissue structures laying on top of each other.

A typical digital mammography apparatus comprises a frame part and a C-arm or a corresponding structure rotatably connected to the frame part. At the first end of the C-arm, there is arranged an x-ray source and at the second end, a radiation detector. A term imaging means is often used for these devices. Disposed substantially in the region between said x-ray source and detector, typically at a close proximity to the detector, a compression structure is arranged which is designed to position a breast as compressed for the duration of an exposure.

Mammography patients often experience varying degrees of anxiety that may be related not only to the general fear regarding a possible disease the examination may discover as such but also, for example, to the fear of physical pain the compressing of a breast for the imaging process or the injecting of a biopsy needle into the breast tissue causes. As the patient's anxiety may affect the patient's behavior, and thus the success of the imaging or sampling, all means by which the patient's fears can be alleviated are welcomed.

User interfaces of the mammography apparatus are traditionally fixed structures and as the name suggests, specifically designed to be used by the user of the apparatus. Traditionally, mammography apparatus have not been arranged with means for presenting information to a patient.

In mammography, it is known to use images taken of the patient earlier or during the ongoing operation as a source of information for taking new images, or for biopsy. It is known to use information one can get from such images to facilitate patient positioning, when the same object is being imaged anew, or when one is about to initiate a biopsy, or during it. According to the prior art, such images taken earlier have been studied at a workstation, which typically has not been arranged immediately next to the mammography apparatus. This means that the information relevant for positioning, established at the workstation, just has to be remembered and figured out correctly after having returned to the mammography apparatus from the workstation.

SUMMARY OF THE INVENTION

The object of the present invention and its preferable embodiments is to accomplish a new kind of mammography apparatus including integrated solutions thanks to which the biopsy operation or the positioning of the breast for the imaging may be facilitated. On the other hand, preferable embodiments of the invention can alleviate the patient's fear relating to an upcoming operation or during it.

The object of the invention is achieved by a solution of the accompanying independent claims. Some preferable embodiments of the invention have been presented in the accompanying dependent claims. It is essential to the invention to implement an arrangement integrated to the mammography apparatus which enables presenting images taken of the patient on a screen, which is arranged to the mammography apparatus in the immediate vicinity of its imaging station.

Thus, a mammography apparatus according to the invention is arranged with a screen (17) or a user interface with a screen (17), which is brought into a functional connection with an information system in which images taken of a patient are recorded. A memory of this information system can comprise a memory arranged in connection with the mammography apparatus or a memory separate to that, or both. When images taken of a patient earlier are studied, according to the prior art, at some separate workstation, the present invention provides an opportunity to bring such images to the immediate vicinity of a place where information one can get from the earlier images can be directly utilized to facilitate positioning. Preferably, the arrangement includes a possibility to present the images taken of the patient earlier in the same orientation in which the breast is being positioned to the imaging apparatus.

On the other hand, preferable embodiments of the invention provide a new way to guide and calm the patient and to provide information to the patient prior to or during an imaging or biopsy procedures. Thanks to embodiments of the invention, the patient can be provided information on when exactly an exposure will begin and the patient should be still, for example, or how long the operation will still last.

According to a further embodiment, a method for positioning a breast to a mammography apparatus is provided. In this method an image taken of the breast is used as an aid for positioning the breast, wherein the image of the breast is a patient image recorded earlier in an information system external to the mammography apparatus. According to the present embodiment, the earlier image is presented on a screen or a user interface with a screen attached to the structure of the mammography apparatus.

According to an additional embodiment, a mammography imaging arrangement is provided. The arrangement includes a frame or a frame part attachable to a wall or a ceiling and an arm structure connected to said frame or frame part and pivotable in relation to a horizontal rotation axis. The arm structure includes an X-ray source and an image data receiving means. The arrangement further includes a control system including a user interface arrangement and at least one screen or user interface with a screen, wherein the control system is connected to an external information system remote from the mammography imaging arrangement such that patient images recorded remote from the mammography imaging arrangement can be displayed on said screen and/or used in positioning the breast and/or the arm structure during imaging.

DETAILED DESCRIPTION OF THE INVENTION

In the following, some embodiments of the invention and their benefits will be described in more detail, also with help of the attached figures, of which figures

DETAILED DESCRIPTION OF THE INVENTION

Figure 1:
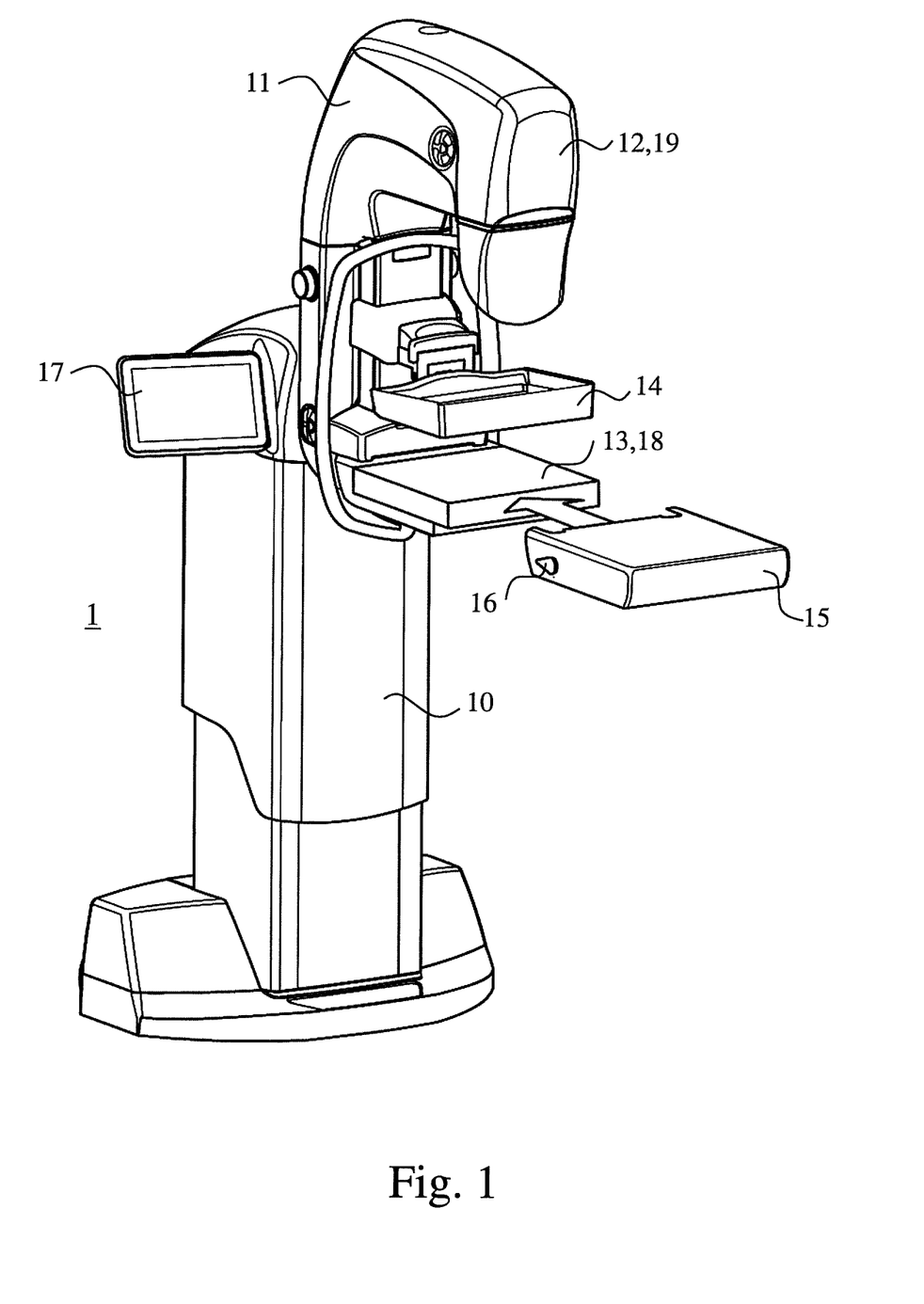
FIG. 1 shows a basic structure of one mammography apparatus according to the invention.

A mammography apparatus (1) presented in FIG. 1 consists of a substantially vertically standing frame part (10) and an arm structure (11) connected to it. An X-ray source (12) is arranged to the upper part of the arm structure (11), within its cover, the x-ray source (12) being arranged to generate a beam which goes through an upper compression plate (14) of the mammography apparatus (when such upper compression plate is connected to the apparatus) and towards a detector (18) placed in a detector housing (13). The detector housing (13) or a corresponding structure is typically arranged inside a lower tray structure (15). The lower tray structure (15) can be a structure fixed to the apparatus or it can be arranged as removably connected. When the upper surface of the lower tray structure (15) typically functions as a platform on which a breast is positioned for imaging, this structure is often also referred to as a lower compression plate. Also, in connection with the arm structure (11), such as in the vicinity of the radiation source (12), a camera or a video camera aligned at the lower tray structure (15) may have been arranged, to be utilized in patient positioning. In the solution according to FIG. 1, attaching means (16) is arranged to the lower tray structure (15) to enable its releasable connection to the mammography apparatus (1). In addition, a screen (17) or a user interface with a screen (17), to be described in more detail below, is arranged to the apparatus according to FIG. 1.

Figure 3A:
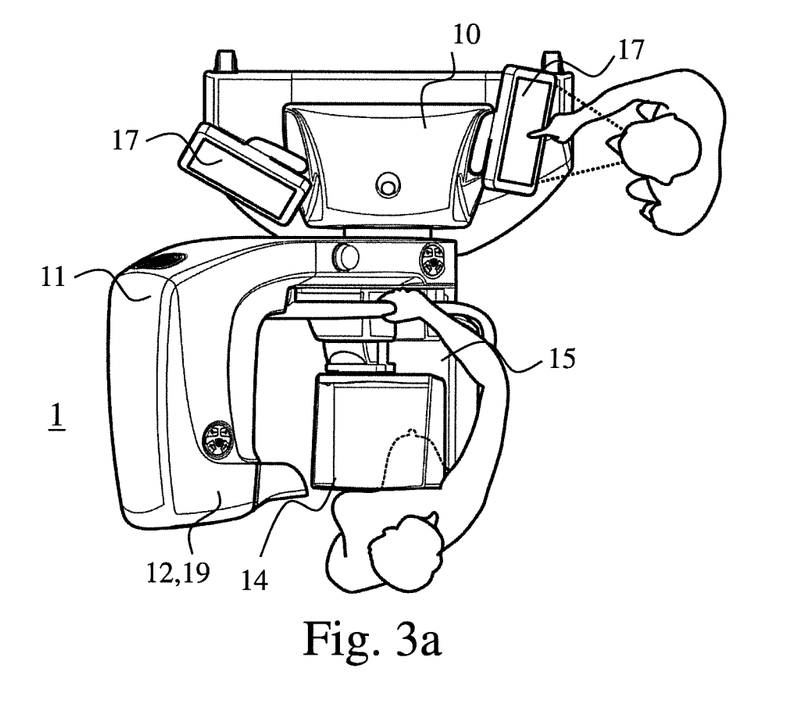
FIGS. 3a, 3b and 3c show a mammography apparatus according to FIG. 1 in an oblique imaging position and as viewed from above.
Figure 3B:
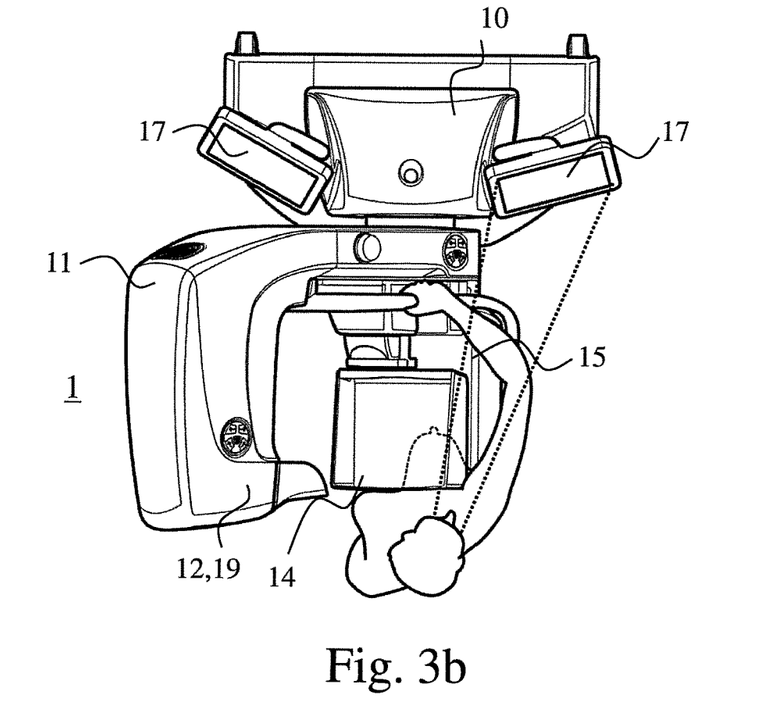
Figure 3C:
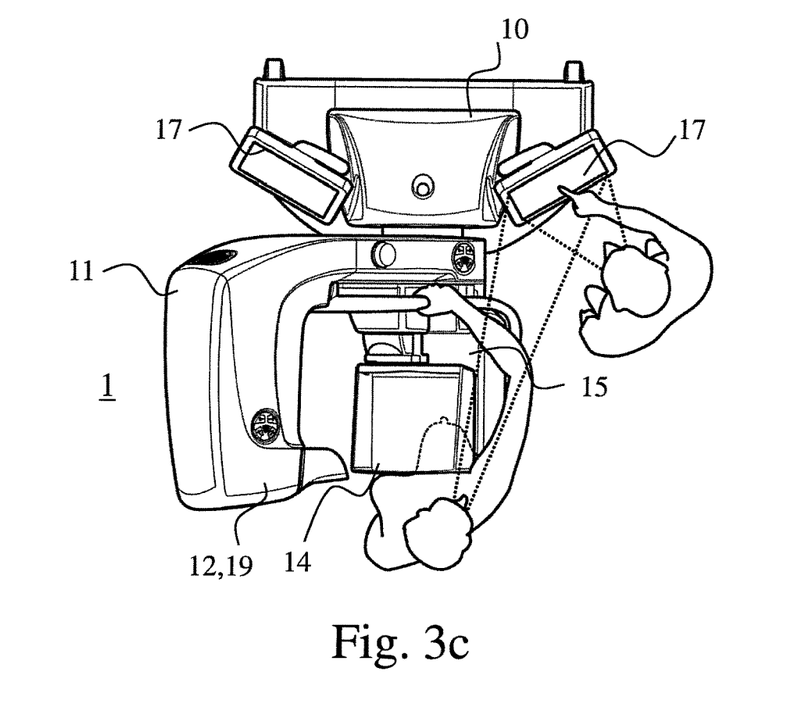

FIGS. 3a-3c show the apparatus according to FIG. 1 as viewed from above and in an oblique imaging position. Two screens (17), which may be touch screens, are arranged to the frame part (10) of the apparatus, on the opposite sides of the frame part (10). Attachment of the screen (17) to the frame part (10) of the apparatus may be articulated such that it can be turned to both a first position in which it is aligned away from the lower tray structure (15) of the apparatus (FIG. 3a), in connection with which structure the patient is positioned for imaging or operations, and to a second position (FIG. 3b) in which it is at least partly aligned towards the lower tray structure (15), i.e. in which it is in such position that the patient has a line of sight to the screen (17).

A position is presented in FIG. 3 intermediate to the previous positions which is applicable for consultation, for example, in which position both the operator of the apparatus and the patient have a good view at the screen (17).

The screen (17) may be just a screen but preferably it is a true traditional touch screen and it may also be some other user interface comprising a screen. Then the first position of the touch screen (17) according to FIG. 3a can be used when operations of the apparatus are controlled or when information is presented on the touch screen which one does not want the patient to see or which the patient needs no to see. Also the position according to FIG. 3b, and especially according to FIG. 3c can be used when controlling operation of the apparatus, but those positions of the screen (17) are especially designed to be used for delivering information to the patient.

Figure 2:
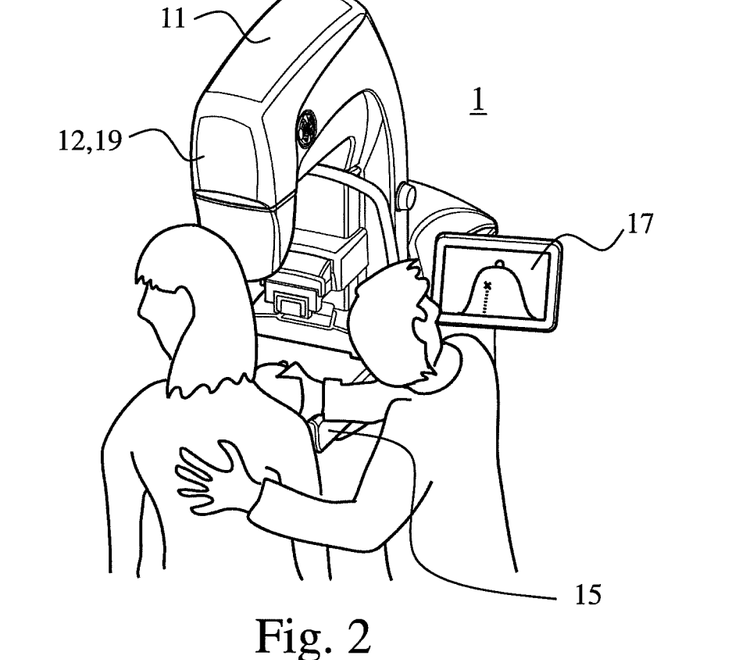
FIG. 2 shows a solution in which information which facilitates patient positioning is being presented on a screen connected to a mammography apparatus.
Figure 4:
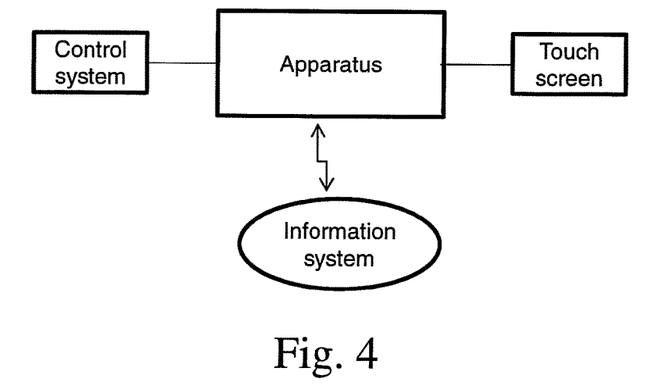
FIG. 4 is a diagrammatic presentation of an arrangement for presenting information in connection with a mammography imaging apparatus.

In reference to FIG. 4, according to one preferable embodiment of the invention, the touch screen (17) is arranged in functional connection with the control system of the apparatus to display imaging parameter values, for example, or the time remaining in the imaging process. Preferably, though, a functional connection like this is arranged e.g. to a patient data base, whereby one preferable embodiment according to the invention includes a solution in which a touch screen (17) is arranged in a functional connection with an information system in which images of a patient taken earlier have been recorded. It is known as such to use information achievable from such images to facilitate patient positioning when the same object is being re-imaged or when a biopsy is to be started or is going on, which information may include measurement markings or other made to the images relating to findings which have been detected. According to prior art, though, such images taken earlier have been studied at some separate workstation, but the present invention makes it possible to bring the images to the immediate vicinity of the place where that information is needed. Then, the arrangement preferably includes a possibility to present images of a patient's breast taken earlier, especially in the same orientation in which the breast is being positioned to the imaging apparatus and in which images, as said, measurement markings or other may have been made relating to findings which have been detected. FIG. 2 demonstrates a situation like this.

Especially the bringing of the touch screen in connection with the imaging station of a mammography apparatus makes it possible to alter characteristics of an earlier image of the breast as well as putting down measurement markings as mentioned above on an image in connection with repositioning.

The screen or the user interface with a screen connected to a mammography apparatus as presented above can be utilized in patient positioning also if the mammography apparatus is equipped with a camera or a video camera (19) aligned at the imaging station of the apparatus. A picture of a breast positioned for imaging may have been taken by such camera (19) in connection with an earlier imaging event (which camera may have in principle been located at some other corresponding apparatus), which picture can then be shown in real time in connection with a new positioning, at the immediate vicinity of the imaging station of the apparatus. On the other hand, also taking a real time photograph of the imaging area may be useful in positioning, when the operator of the apparatus can have a look at the screen to review the positioning situation, instead of following the situation in a possibly cramped space outlined by the mammography apparatus and the patient.

When information one can acquire from prior images is directly available in connection with patient positioning, such as information of location of a finding detectable from earlier images, the present invention provides a possibility for smooth and precise positioning for re-imaging or biopsy. Further, the possibility to guide and inform the patient of various stages of the imaging or biopsy event can help in achieving a successful procedure, by e.g. helping the patient to be still throughout an operation which may take quite a while.

According to one alternative embodiment of the invention, the imaging arrangement comprises a means with the help of which images of patients are recorded with identifiers such as patient identification, examination time, imaging modality and imaging procedure description. Such prior images can then be identified based on the identifiers and be automatically retrieved from the information system by image retrieval means for subsequent scheduled procedures, to be presented as positioning guides when new images are being acquired.

Moreover, prior mammography image(s) can be automatically loaded on a touch screen display of the workstation of the mammography imaging device based on choices made regarding the imaging procedure(s) to be performed. For example, the mammography operator may be presented investigation options, such as a work list, a study opened for a patient, a selected imaging mode, the breast that has been selected, or projection(s). The present system can automatically select appropriate prior images based on the selected option(s). As such, the present embodiment provides a user with a workflow which is simpler with less reliant on memory than prior methodology. More particularly, useful prior images can be automatically depicted on the touch screen and/or display of the mammography apparatus based on the imaging to be performed.

According to one alternative embodiment, the prior image is automatically made available as a positioning guide at a screen of the imaging apparatus according to imaging parameters to be used. The imaging parameter may be e.g. a selected imaging view and the prior image of the corresponding view can be made automatically available. The arrangement may thus include a means to be continuously aware of or to recognize on demand the acute orientation of the arm structure (11) supporting the x-ray source (12) and the detector housing (13) and a means to correlate information of the acute orientation with a prior image with an orientation identifier corresponding to the acute orientation of the arm structure (11).

According to one further embodiment, the prior image to be presented on a screen is automatically adjusted so as to not present irrelevant information. For example, the prior image can be presented as zoomed or cropped to only show the relevant and/or visible anatomy. In this regard, the present embodiment automatically can provide an otherwise full size mammography image in a size fitted to a touch screen used during the imaging process itself. In one specific embodiment, cropping or zooming of the prior image is automatically performed such that the system automatically maintains the main point(s) of interest of the area to be imaged. Similarly, if there is labeling in the prior image, such as items that have been marked, these can be used as automatic markers so that these marked items (and optionally some of the surrounding area) are captured in the imaging being performed. Furthermore, it is contemplated that the present mammography arrangement may rotate (e.g. 90°) prior images received from a typical workstation orientation to a map mode so that the displayed image corresponds in orientation to a positioning orientation of the breast associated to the mammography device.

Figure 5:
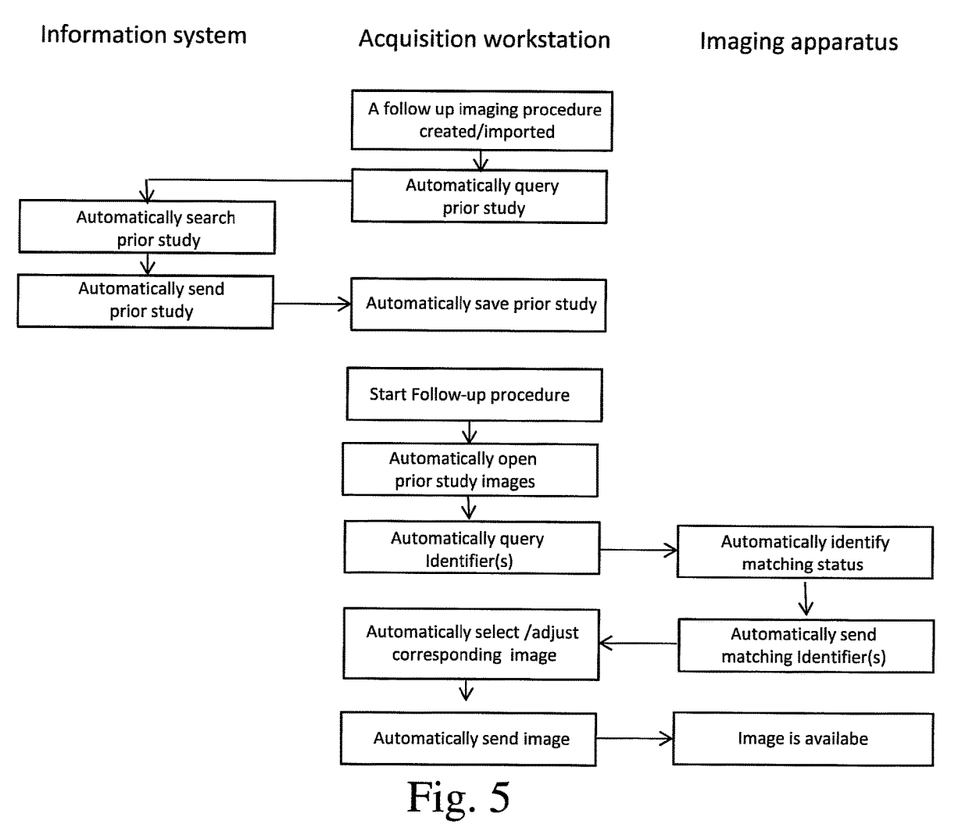
FIG. 5 is a flow chart of an automated image retrieval process applicable for use in connection with the invention.

FIG. 5 shows one exemplary procedure to realize the automated prior image acquisition. When a follow up imaging of a patient is to be performed, an automated search from the information system is made for any related prior images (prior studies) which are then stored at a workstation. An exemplary work station can include a data input mechanism, a monitor, and a computer processor (optionally remotely located). Upon initiation of the follow up imaging procedure, identifiers of the images of the previous study are compared with positioning status at the imaging apparatus and in case a prior image at least generally corresponding to the current positioning is found, the image thus acquired is shown on a screen at the imaging apparatus, possibly as adjusted as discussed above.

Depending on the system available, the initial steps according to FIG. 5 relating to first separately acquiring and storing the prior information may not be needed.

The invention can also be realized by the patient herself controlling operation of the mammography apparatus from the user interface brought in connection with the imaging station when the patient's breast is being compressed for imaging. Such solution is prone to lessen the fears of the patient relating to compressing a breast, taking in consideration that there are studies according to which a patient may allow the mammography apparatus to compress a breast even more when she can control the compressing process herself. The solution according to the invention may thus offer the possibility to bring a touch screen (17) arranged to control operation of the mammography apparatus so close to the lower tray structure (15) of the apparatus that the patient can herself control via it e.g. movements of the upper compression plate (14) of the apparatus according to FIG. 1.

In one embodiment of the invention the articulation of the screen (17) or the user interface with a screen (17) is realized as motorized. Then, at least one operation mode can be arranged to the control system of the apparatus according to which the screen (17) automatically turns into a position which has been designated for it in that operation mode. The position of the screen (17) can thus be arranged to be changed according to which procedure that operation mode relates to, or according to what the control system displays on the screen. The screen (17) can be arranged e.g. to turn towards the patient when the time remaining in the image process is displayed on the screen. On the other hand, also in the case of an articulation being implemented to be turned manually, one or more views may be defined in the control system which are automatically displayed on the screen when it is turned into a position in which it comes to the field of view of the patient, i.e. into a position as aligned towards the lower tray structure (15).

Solutions according to the invention and its preferable embodiments may thus include a mammography apparatus which includes a substantially vertically standing frame part (10) or a frame part (10) attachable to a wall or a ceiling, an arm structure (11) connecting to this frame part (10) and pivotable in relation to a horizontal rotation axis, at a substantially first end of the opposite ends of the arm structure (11) is placed an X-ray source (12), and substantially at a second end an image data receiving means (18), and in connection with said second end of the arm structure (11) is additionally arranged a lower tray structure (15) positioned substantially on top of the image data receiving means (18), a control system and in connection with it a user interface arrangement and at least one screen (17) or user interface with a screen (17). Said screen (17) or user interface with a screen (17) is connected to the mammography apparatus (1) and the connection is realized such that the screen (17) or user interface with a screen (17) is aligned or can be aligned at least partly towards the lower tray structure (15). Further, a means is arranged to the mammography apparatus (1) to bring said screen (17) or user interface with a screen (17) into a functional connection with an external information system such that patient images recorded earlier in said information system can be displayed on said screen (17) or user interface with a screen (17) connected to structures of the mammography apparatus. Preferably the arrangement includes a means for showing images on the screen (17) in an orientation corresponding to an orientation in which a breast is positioned on top of said lower tray structure (15).

As patient positioning in mammography typically includes procedures performed on both sides of the lower tray structure, the invention gets effectively utilized when said screens (17) or user interfaces with a screen (17) are arranged to the mammography apparatus (1) at least one on both of its sides, as viewed from said lower tray structure (15).

The user interface arrangement may include at least one screen (17) or user interface with a screen (17) which is
attached as articulated to the frame part (10) or
implemented with a technology by which a direction in which information on the screen is visible is adjustable
so that a view generated by said at least one screen (17) or a user interface with a screen (17) can be aligned at least at a first direction in which it is aligned away from said lower tray structure (15) and at a second direction in which it is at least partially aligned towards said lower tray structure (15).

The at least at least one screen (17) or user interface with a screen (17) is attached to the frame part (10) as articulated. The articulation can be realized as motorized and said control system to comprise at least one operation mode according to which a view generated by the screen automatically turns into a position determined for it by said operation mode, as dependent on the operation to which the operation mode relates to or on what the control system shows on the screen (17). The articulation can also include a structure which enables bringing the screen (17) or the user interface with a screen into a substantial vicinity of the lower tray structure (15), especially within an arm's length or closer.

One or several views can be defined in the control system to be automatically presented on the screen (17) or a user interface with a screen (17), when it is turned into its said second position.

The invention also concerns a method for positioning a breast into a mammography apparatus, in which method an image taken of the breast is used as an aid for positioning the breast, which image is a patient image recorded earlier in an information system external to the mammography apparatus and said image is presented on a screen (17) or a user interface with a screen (17) attached to the structures of the mammography apparatus. This image can be presented in a direction at which there is a line of sight from an imaging station of the mammography apparatus, especially in an orientation corresponding to the orientation in which the breast is being positioned for mammography imaging or for biopsy, in relation to the imaging station of the mammography apparatus.

The invention claimed is:

1. A mammography imaging arrangement which includes a mammography apparatus and which comprises
    a substantially vertical standing frame or a frame part attachable to a wall or a ceiling,
    an arm structure connected to said frame or frame part and pivotable in relation to a horizontal rotation axis,
    the arm structure including an X-ray source and an image data receiving means, and
    a control system comprising at least one touch screen with a user interface secured to the mammography imaging arrangement, wherein said control system is connected to an external information system remote from the mammography imaging arrangement such that a patient image recorded remote from the mammography imaging arrangement and modified to include measurement or other markings which relate to findings which have been detected can be displayed on said screen and used in positioning a breast for an imaging process, and wherein the patient image of the breast is first recorded and displayed on said external information system and later displayed with the measurement or other markings as on the screen of the control system.

2. The arrangement of claim 1, wherein a patient identifier is added to the image displayed on said external information system.

3. The arrangement of claim 2, wherein said patient image includes a patient identifier selected from patient identification, examination time, imaging modality and imaging procedure description.

4. The arrangement of claim 3, wherein said patient identifier functions as a positioning guide for the arm structure during imaging.

5. The arrangement of claim 1, wherein said patient image recorded remote from the mammography imaging arrangement is zoomed, cropped and/or rotated on said screen.

6. The arrangement of claim 1, further including a camera or video camera allowing an earlier breast image to be shown on the touch screen in real time in connection with a breast positioning image.

7. The arrangement of claim 1, wherein said external information system comprises a workstation at which the marking can be applied to the patient image.

8. The arrangement of claim 1, wherein said patient image is taken at a different mammography imaging apparatus.

* * * * *